United States Patent
Bahrmann et al.

[11] Patent Number: 5,801,291
[45] Date of Patent: Sep. 1, 1998

[54] PROCESS FOR THE PREPARATION OF ALDEHYDES BY MEANS OF A CATALYST SYSTEM COMPRISING RHODIUM AND SUBSTITUTED DIPHENYLDIPHOSPINES

[75] Inventors: Helmut Bahrmann, Hamminkeln; Hans-Jerg Kleiner, Kronberg; Dieter Regnat, Eppstein, all of Germany

[73] Assignee: Hoechst AG, Germany

[21] Appl. No.: 813,877

[22] Filed: Mar. 7, 1997

[30] Foreign Application Priority Data

Mar. 11, 1996 [DE] Germany ............... 196 09 337.6

[51] Int. Cl.⁶ ........................................... C07C 45/50
[52] U.S. Cl. .................................. 568/454; 568/451
[58] Field of Search ........................ 568/451, 454

[56] References Cited

U.S. PATENT DOCUMENTS

| | | | |
|---|---|---|---|
| 4,248,802 | 2/1981 | Kuntz | 568/454 |
| 5,174,899 | 12/1992 | Bahrmann et al. | 210/644 |

FOREIGN PATENT DOCUMENTS

| | | |
|---|---|---|
| 0374615 | 6/1990 | European Pat. Off. |
| 2627354 | 12/1980 | Germany |

OTHER PUBLICATIONS

Toth et al; Tetrahedron Asymmetry; vol. 1,#12,pp.913–930, 1990.
Toth et al; Tetrahedron Asymmetry; vol. 1,#12,pp.895–912, 1990.
Toth et al; Organometallics;vol. 12,#3,pp.848–852, 1993.
Toth et el; Organometallics;vol. 12,#5, pp.1506–1513, 1993.

*Primary Examiner*—Gary Geist
*Assistant Examiner*—Sreeni Padmanabhan
*Attorney, Agent, or Firm*—Connolly & Hutz

[57] ABSTRACT

The present invention relates to a process for the preparation of aldehydes, which comprises reacting an olefinic compound having 2 to 20 carbon atoms with carbon monoxide and hydrogen, in the presence or absence of a solvent, in the presence of a catalyst comprising rhodium and a compound or a mixture of compounds of the formula (I)

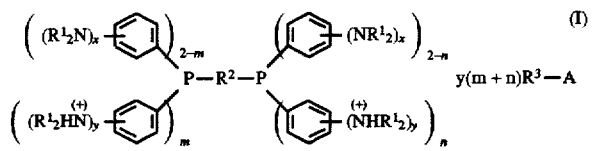

in which $R^1$ is H or an alkyl radical having 1 to 12 carbon atoms, $R^2$ is a straight-chain alkylene radical having 1 to 8 carbon atoms, an oxygen-containing alkylene radical having 2 to 4 carbon atoms, a radical of the formula (II) or (III)

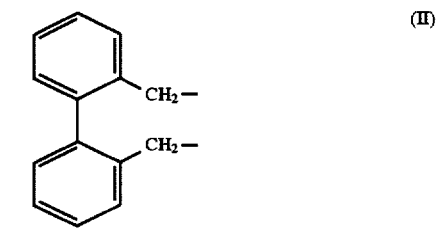

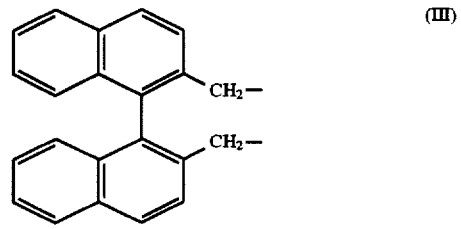

or a cycloalkylene radical having 3 to 10 carbon atoms, $R^3$ is an alkyl radical having 1 to 25 carbon atoms or an aryl radical having 6 to 10 carbon atoms, A is a radical —COO⁻ or —SO₃⁻ and x=0, y=1, m=1 and n=1, or x=0.1, y=1, m=(1 or 2) and n=(1 or 2), or, if $R^2$ is a radical of the formula (II) or (III), x=1, y=0, m=(0 or 1) and n=(0 or 1), at a temperature from 50° to 190° C. and under a pressure from 0.1 to 45 MPa, and separating the reaction product off from the catalyst.

20 Claims, No Drawings

PROCESS FOR THE PREPARATION OF ALDEHYDES BY MEANS OF A CATALYST SYSTEM COMPRISING RHODIUM AND SUBSTITUTED DIPHENYLDIPHOSPINES

The present invention relates to a process for the preparation of aldehydes by reaction of olefinic compounds with hydrogen and carbon monoxide under elevated pressure in a homogeneous phase and in the presence of a catalyst system comprising rhodium and novel substituted diphenyldiphosphines and separation of the reaction product from the catalyst.

It is known that aldehydes and alcohols can be prepared by reaction of olefins with carbon monoxide and hydrogen. The reaction is catalyzed by hydrido-metal carbonyls, preferably those of metals of group 8 of the periodic table. In addition to cobalt, which is widely used industrially as a catalyst metal, rhodium has recently acquired increasing importance. In contrast to cobalt, rhodium enables the reaction to be carried out under a low pressure; furthermore, straight-chain n-aldehydes are preferentially formed, and only minor amounts of iso-aldehydes. Finally, hydrogenation of the olefins to saturated hydrocarbons also takes place to a significantly lesser extent using rhodium catalysts than if cobalt catalysts are used.

In the processes introduced in the art, the rhodium catalyst is employed in the form of modified hydrido-rhodium carbonyls, which comprise additional ligands that are employed in excess if appropriate. Tertiary phosphines or phosphites have proven particularly suitable as ligands. Their use enables the reaction pressure to be reduced to values below 30 MPa.

In this process, separating off the reaction products and recovering the catalysts dissolved homogeneously in the reaction product are problematic. In general, the reaction product is distilled off from the reaction mixture for this purpose. In practice, however, this path can be taken only in the case of hydroformylation of lower olefins, i.e. olefins having up to about 5 carbon atoms in the molecule, because of the sensitivity of the aldehydes and alcohols formed to heat.

During hydroformylation of long-chain olefins or olefinic compounds having functional groups, products having a high boiling point are formed which cannot be separated off by distillation from the homogeneously dissolved rhodium complex catalyst. Exposure of the distillation material to heat leads to considerable losses of valuable products, owing to formation of thick oil, and of catalyst, owing to decomposition of the rhodium complex compounds.

Separating off the catalyst by a thermal route is avoided by using water-soluble catalyst systems. Such catalysts are described, for example, in DE-C 26 27 354. The solubility of the rhodium complex compounds is achieved here by using sulfonated triarylphosphines as the complexing constituent. In this process variant, the catalyst is separated off from the reaction product when the hydroformylation reaction has ended simply by separation of the aqueous and organic phase, i.e. without distillation and therefore without additional thermal process steps. Another feature of this procedure is that n-aldehydes are formed from terminal olefins with a high selectivity, and iso-aldehydes are formed only to a very minor extent. In addition to sulfonated triarylphosphines, carboxylated triarylphosphines are also employed as complexing constituents of water-soluble rhodium complex compounds.

The use of water-soluble catalysts has proven excellent for the hydroformylation of lower olefins, in particular ethylene and propylene. If higher olefins such as hexene, octene or decene are employed, however, the conversion and/or the selectivity of the reaction to give n-compounds decrease noticeably. The reaction is then often no longer economic on an industrial scale.

Another advantageous method of separating off the catalyst from the product comprises separating the organometallic coordination complexes from organic liquids by a separating membrane having a selective action.

Such a process is described in EP 03 74 615. The organic solution comprising the catalyst is brought into contact with a semipermeable membrane of an aromatic polyamide (polyaramid). Either a pressure difference (pressure filtration) or concentration difference (dialysis) can serve here as the driving force for the separation operation.

Trivalent organophosphorus compounds, in particular phosphines, have proven suitable ligands for metal complex-catalyzed hydroformylation. These phosphines are monophosphines which have sulfonate or carboxylate groups, i.e. anionic phosphines. The associated cations are derived from secondary or tertiary amines which carry long-chain alkyl radicals.

A disadvantage of using these monophosphines as the catalyst constituent is that the monophosphines have to be employed in a comparatively high excess, based on the transition metal, for example rhodium. On the one hand this is uneconomical, and on the other hand it leads to a high salt concentration in the reaction mixture. Under certain circumstances, a high salt concentration can adversely influence the reaction of the olefin with carbon monoxide and hydrogen, since a high salt concentration impairs the solubility of the reaction partners in the reaction mixture and can also promote foaming. Furthermore, a high salt concentration has an adverse effect during separation of the catalyst, because it leads to an increased content of salt-containing thick oil in the case of separation by distillation, or considerably reduces the throughput of the semipermeable membrane in the case of pressure filtration.

There is therefore interest in providing a process for the preparation of aldehydes which does not have the disadvantages described above and can be realized without great expenditure. Furthermore, the catalyst system used should have quite a high activity and render the desired product accessible in a good yield. Moreover, the catalyst system should have an adequate life and should be suitable for further use after being separated off from the reaction mixture.

This object is achieved by a process for the preparation of aldehydes. The process comprises reacting an olefinic compound having 2 to 20 carbon atoms with carbon monoxide and hydrogen, in the presence or absence of a solvent, in the presence of a catalyst comprising rhodium and a compound or a mixture of compounds of the formula (I)

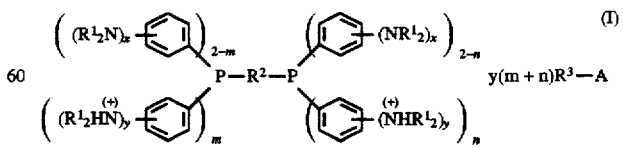

in which $R^1$ is H or an alkyl radical having 1 to 12 carbon atoms, $R^2$ is a straight-chain alkylene radical having 1 to 8 carbon atoms, an oxygen-containing alkylene radical having 2 to 4 carbon atoms, a radical of the formula (II) or (III)

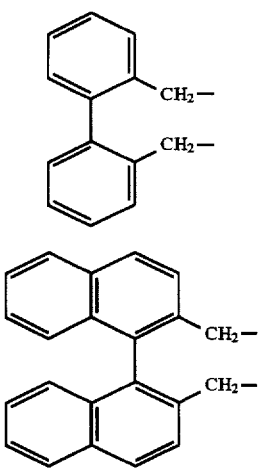

or a cycloalkylene radical having 3 to 10 carbon atoms, $R^3$ is an alkyl radical having 1 to 25 carbon atoms or an aryl radical having 6 to 10 carbon atoms, A is a radical —COO⁻ or —SO₃⁻ and x=0, y=1, m=1 and n=1, or x=1, y=1, m=(1 or 2) and n=(1 or 2), or, if $R^2$ is a radical of the formula (II) or (III), x =1, y=0, m=(0 or 1) and n=(0 or 1), at a temperature from 50° to 190° C. and under a pressure from 0.1 to 45 MPa, and separating the reaction product off from the catalyst.

One advantage of the process according to the invention is that it is easy to manipulate in respect of separating off the catalyst. For example, aldehydes having comparatively low boiling points can be separated off by distillation. Nevertheless, it is also possible to convert the catalyst into a water-soluble form by conversion into another salt, and to separate it off by extraction in an aqueous phase. Another interesting possibility is opened up by separating off the catalyst from the reaction product in a particularly gentle manner by means of membrane filtration (pressure filtration). In this case, the reaction product is passed over a suitable membrane under pressure and the hydroformylated product is separated off as the permeate, while the catalyst and ligand become highly concentrated as salts in the retained material.

Another advantage of the process according to the invention is that the compound of the formula (I), which serves as a catalyst constituent and, optionally, as ligand employed in excess, can be influenced in its properties by varying the radicals $R^3$-A and by varying the nature of these radicals. Long-chain or bulky radicals $R^3$ are of advantage if the catalyst is separated off by means of membrane filtration, since they promote the retention capacity of the membrane and reduce permeation through the membrane.

Furthermore, the process according to the invention enables comparatively small amounts of rhodium and a comparatively low ratio of the compound of the formula (I): Rh to be used. This is proof that the catalyst has a high reactivity, but at the same time also a high stability, under reaction conditions. These advantageous properties are also retained, as can be seen from Example 2, if the used catalyst which has been separated off by membrane filtration is reused.

As mentioned above, an olefinic compound having 2 to 20, in particular 6 to 18, preferably 8 to 16, carbon atoms, which can have one or more olefinic double bonds, is usually employed in the process according to the invention. The olefinic compound can be aliphatic, cycloaliphatic or araliphatic.

Examples of aliphatic compounds are straight-chain and/or branched olefins with a terminal and/or internal position of the double bond. Straight-chain olefins having 2 to 20 carbon atoms, such as ethene, propene, but-1-ene, pent-1-ene, n-hex-1-ene, n-hept-1-ene, n-oct-1-ene, n-non-1-ene, n-dec-1-ene, n-undec-1-ene and n-dodec-1-ene, acyclic terpenes and branched olefins, such as diisobutylene, tripropylene, tetrapropylene and dimersol, are particularly suitable.

Examples of aliphatic dienes are 1,3-butadiene, 1,5-hexadiene and 1,9-decadiene. Examples of cycloaliphatic starting substances are cyclohexene, cyclooctene, cyclooctadiene, dicyclopentadiene and cyclic terpenes, for example limonene, pinene, camphorene and bis abolene, in particular dicyclopentadiene. Styrene is an example of araliphatic olefins.

Olefinic compounds having functional groups which may be mentioned are acrylic acid derivatives, in particular esters, methacrylic acid derivatives, in particular esters, allyl compounds, in particular alcohols and esters, vinyl compounds, in particular esters and ethers, cyano compounds, in particular acrylonitrile, and acrolein derivatives.

The olefinic compounds listed above are merely a selection, with no claim to completeness.

The catalyst comprises rhodium and a compound of the formula (I) or a mixture of compounds of the formula (I). These mixtures of the compounds of the formula (I) often form in the course of the preparation, for example on introduction of the acid radicals $R^3$-A. The reaction of the as yet unprotonated bisphosphine containing amine groups with the acids containing the acid radicals $R^3$-A usually leads to a mixture of corresponding salts.

A compound of the formula (I) in which x=0, y=1, m=1 and n=1, or x=1, y=1, m=(1 or 2) and n=(1 or 2), in particular x=1, y=1, m=(1 or 2) and n=(1 or 2), or a mixture of these compounds, is usually employed.

In the compound of the formula (I), the $R^1{}_2N$- and $R^1{}_2NR^+$- group can be in any desired position on the particular benzene ring. A compound of the formula (I) in which the $R^1{}_2N$- and the $R^1{}_2NH^+$-group are in the meta- or para-position, in particular in the para-position, relative to the bond which joins the benzene ring to the particular P atom, or a mixture of these compounds, is expediently employed.

A compound of the formula (I) in which $R^1$ is an alkyl radical having 1 to 4 carbon atoms, in particular a methyl or ethyl radical, preferably a methyl radical, or a mixture of these compounds, is employed because of their relatively good accessibility and availability.

The process can be carried out with good success using a compound of the formula (I) in which $R^2$ is an alkylene radical having 1 to 4 carbon atoms or a radical —(CH₂)₂—O—(CH₂)₂—, in particular a trimethylene or tetramethylene radical, or using a mixture of these compounds.

In a large number of cases, it has proved favorable to employ a compound of the formula (I) in which $R^3$ is an alkyl radical having 12 to 24 carbon atoms or an aryl radical having 6 or 7 carbon atoms, in particular an alkyl radical having 14 to 22 carbon atoms, or a mixture of these compounds.

As already mentioned above, A is a radical COO⁻ or SO₃⁻, in particular a radical COO⁻. A mixture of such compounds of the formula (I) can also be employed.

In a number of cases, the process according to the invention can be carried out with comparatively small amounts of rhodium. However, it can also be carried out with relatively large amounts of rhodium. In general, the reaction is carried out in the presence of 5 to 500, in particular 10 to 150, ppm of rhodium, based on the olefinic compound.

The ratio of the compound of the formula (I) to rhodium can be varied within quite wide limits. The compound of the formula (I) and rhodium are usually employed in a ratio of 1:1 to 200:1, in particular 2:1 to 10:1 (mol of compound of the formula (I) per g atom of rhodium).

A rhodium compound, for example a rhodium salt, is usually used for preparation of the catalyst. Suitable rhodium salts, with no claim to completeness, are rhodium chloride, rhodium sulfate, rhodium nitrate and rhodium carboxylates, such as rhodium acetate, rhodium propionate, rhodium butyrate and rhodium 2-ethylhexanoate.

The rhodium compound is brought together with the compound of the formula (I) and a solution of the mixture of the two substances is prepared. Suitable solvents are organic solvents which are inert under the hydroformylation conditions. These include, inter alia, aromatic hydrocarbons, for example toluene, ortho-xylene, meta-xylene, para-xylene, mixtures of isomeric xylenes, ethylbenzene, mesitylene and mixtures of these compounds, aliphatic hydrocarbons, such as hexane or octane, or else cycloaliphatic hydrocarbons, such as cyclohexane.

However, the olefinic compound and the hydroformylation product can also be used as the solvent for the catalyst.

The solution of the rhodium compound and of the compound of the formula (I) can be employed directly in the hydroformylation, or the catalyst can be preformed beforehand and then employed in the reaction.

As already explained above, the process according to the invention is suitable for the hydroformylation of a large number of olefinic compounds. For example, a substituted or unsubstituted alkene having 2 to 20 carbon atoms, a substituted or unsubstituted diene having 4 to 10 carbon atoms, a substituted or unsubstituted cycloalkene or dicycloalkene having 5 to 12 carbon atoms in the ring system, an ester of an unsaturated carboxylic acid having 3 to 20 carbon atoms and an aliphatic alcohol having 1 to 18 carbon atoms, an ester of a saturated carboxylic acid having 2 to 20 carbon atoms and an unsaturated alcohol having 2 to 18 carbon atoms, an unsaturated alcohol or ether having in each case 3 to 20 carbon atoms or an araliphatic olefin having 8 to 20 carbon atoms can be employed as the olefinic compound.

The reaction temperature also depends to a certain extent on the nature of the olefinic compound which is to be reacted. Comparatively reactive olefinic compounds can be reacted at relatively low temperatures, while comparatively unreactive olefinic compounds require relatively high temperatures.

In general it is sufficient, as mentioned above, to allow the reaction to proceed at a temperature of 50° to 190° C. In many cases, it has proven appropriate to carry out the reaction at 80° to 180° C., in particular 100° to 170° C. It can also be carried out at temperatures below 50° C., but in this case prolonged reaction times must be accepted. It is also possible to carry out the reaction above 190° C., but in this case an increased formation of by-products, such as hexane, octane or else cycloaliphatic hydrocarbons, such as cyclohexane, must possibly be expected.

The reaction proceeds under pressure in the presence of carbon monoxide and hydrogen. Carbon monoxide and hydrogen can be employed in a molar ratio of 5:1 to 1:5, in particular 2:1 to 1:2, preferably 1.2:1 to 1:1.2.

It is often sufficient to carry out the reaction under a pressure of 1 to 35 MPa, in particular 3 to 30 MPa. Since a high pressure as a rule promotes the reaction, the reaction is carried out at relatively high pressures, for example above 15 MPa, in particular above 20 MPa, in a large number of cases. This procedure will be preferred if suitable pressure containers are available.

The process can be carried out in the presence or absence of an organic solvent which is inert under the hydroformylation conditions. Suitable solvents are aromatic hydrocarbons, for example toluene, ortho-xylene, meta-xylene, para-xylene, mixtures of isomeric xylenes, ethyl benzene or mesitylene, aliphatic hydrocarbons, for example hexane or octane or else cycloaliphatic hydrocarbons, and mixtures of these compounds.

However, in a number of cases it is possible to omit the use of an organic solvent. In these cases, the olefinic compound and the hydroformylation product formed assume the role of a solvent.

When the reaction has ended, the reaction product is cooled and is freed from gaseous constituents by being let down. The reaction mixture obtained in the reaction is then separated off from the catalyst by means of distillation, extraction or pressure filtration.

The method chosen for separating off the mixture depends on the nature of the hydroformylation product. Hydroformylation products which are relatively heat-stable and do not have very high boiling points can be separated off from the catalyst by distillation, for example under reduced pressure.

Removal of the catalyst by extraction will be preferred if it is possible, for example, to convert the catalyst into a water-soluble form and separate it off as an aqueous phase by means of an extraction with an acceptable expenditure. Gentle separation of the catalyst from the reaction mixture can be achieved in this manner. From the aqueous phase, the catalyst can be converted back into a water-insoluble form suitable for further use, optionally by conversion into another salt.

According to a particular process variant, the reaction mixture is separated off by pressure filtration by means of a semipermeable membrane, in particular by means of a polyamide (nylon) membrane, preferably by means of a polyaramid membrane. In this case, the reaction mixture is passed over the membrane under pressure, for example 1 to 5 MPa, to give a permeate which is essentially free from the catalyst, while the catalyst becomes highly concentrated in the retained material (retentate).

The retentate comprising the catalyst can be combined and re-used in the process, optionally after pre-forming and optionally after topping up with fresh catalyst. Multiple re-use is possible without having to accept noticeable losses in respect of activity and selectivity of the catalyst, and pre-forming (additional treatment with carbon monoxide and hydrogen) and also addition of fresh catalyst (rhodium and/or compound of the formula (I)) can usually be omitted. Handling of the catalyst in the active state is generally to be carried out with exclusion of air, since even very small amounts of oxygen damage the catalyst, or deactivate it irreversibly. Oxidation of P(III) to P(V) in the compound of the formula (I) is probably primarily responsible for this.

For completeness, it should be pointed out here that the compounds of the formula (I) and their preparation are the subject matter of German Patent Application (File number 196 093 36.8) filed on the same day as the present Patent Application.

The following Examples demonstrate the invention without limiting it thereto.

Experimental section

EXAMPLE 1

Pre-forming of the catalyst 550 g of toluene freed from oxygen are initially introduced into a glass receiver under a nitrogen atmosphere, and 0.53 g of 1,4-bis[bis(4-dimethyl-aminophenyl)phosphino]butane×2 palmitic acid and 0.19 mmol of rhodium in the form of Rh 2-ethylhexanoate are added, while stirring. The resulting toluene solution is transferred under a nitrogen atmosphere into a 5 l autoclave, with a stirrer, which has been flushed thoroughly with nitrogen. A pressure of 270 bar [27 MPa] is established by forcing in synthesis gas, while stirring, and the mixture is heated up to 125° C. and allowed to react for 2 hours. This completes the pre-forming of the catalyst.

Hydroformylation

When the pre-forming has ended, a total of 1300 g of propylene are pumped from a pressurized receiver into the autoclave under a pressure of 270 bar [27 MPa] at 125° C. in the course of 1.5 hours. The pressure is kept at 270 bar by forcing in synthesis gas. The reaction temperature is 125° C., the excess heat released by the hydroformylation being removed by means of cooling (air fan). The hydroformylation proceeds in the presence of 15 ppm of rhodium, based on the total propylene employed. The ratio of 1,4-bis[bis(4-dimethylaminophenyl)phosphino]butane×2 palmitic acid to rhodium is 2.5:1 (corresponding to a ratio of P:Rh=5:1). After the end of pumping, the mixture is allowed to after-react for another hour, and the autoclave is then cooled and let down in the course of 1.5 hours.

The content of the autoclave are emptied under the remaining residual pressure into a 6 l three-necked flask with immersion connectors and weighed (2630 g). A propylene conversion of 92% is calculated from the weight increase. Taking into account the losses which occur during letting down of the autoclave, this corresponds to an almost complete conversion.

The crude product comprises:
- 8.74 ppm of Rh
- 118 ppm of P (total)
- 1.6 mmol of P(III)/kg
- 34.0 mg of total basic nitrogen (in glacial acetic acid)/kg

Membrane filtration (pressure filtration)

2541 g of the crude product obtained from the hydroformylation are . . . via a laboratory membrane filter unit (M 577/579=designation ?). A polyaramid membrane (VF-PA5/PET 100; a product from Hoechst AG), which has been conditioned at 100° C. in water for 15 minutes before use, is used as the membrane. The crude product is allowed to flow over the membrane at 150 l/hour under a pressure of 15 bar [1.5 MPa] by means of a circulating pump. 93% of the crude product passes through the membrane as permeate. 149.2 g remain as concentrated retentate, comprising rhodium and the 1,4-bis[bis(4-dimethylaminophenyl)phosphino]butane×2 palmitic acid.

The permeate comprises:
- 0.25 ppm of Rh
- 15.0 ppm of P (total)
- 0.9 mmol of P(III)/kg
- 16.0 mg of total basic nitrogen/kg The flow capacity decreases during the membrane filtration (pressure filtration) from initially 77.5 l/m²×hour to 49.1 l/m²×hour. The decrease in the flow capacity is caused by the progressive concentration of the retentate.

The total permeate is subjected to a second membrane filtration (pressure filtration) under the same conditions as described above. The amount of retentate is 141.6 g.

The permeate comprises:

|  | Retention* |
| --- | --- |
| 0.21 ppm of Rh | 97.65% |
| 6.6 ppm of P (total) | 94.41% |
| 1.00 mmol of P(III)/kg | 37.5% |
| 11.00 mg of total basic nitrogen (in glacial acetic acid)/kg | |

*The retention relates to the amounts originally employed.

The flow capacity drops during the membrane filtration (pressure filtration) from initially 84 l/m²×hour to 81.4 l/m²×hour.

EXAMPLE 2

Hydroformylation with reuse of the catalyst

The catalyst-containing retentate (149.2 g+141.2 g from Example 1) is initially introduced into the reaction vessel under a nitrogen atmosphere and is topped up to a total of 550 g with toluene, a pressure of 270 bar is established by forcing in synthesis gas, while stirring, and the mixture is heated up to 125° C.

The hydroformylation is then carried out by addition of 1300 g of propylene in the course of 1.5 hours, as described in Example 1. The resulting crude product is subjected to a membrane filtration (pressure filtration) and the combined retentate comprising the catalyst is re-used again, the hydroformylation being carried out as described above with 1300 g of propylene, which is pumped in over a period of 1.5 hours, under a pressure of 270 bar at 125° C. A propylene conversion of 95.6% is calculated from the weight increase of the reaction product obtained after the catalyst has been reused a second time (retentate from the membrane filtration).

COMPARISON EXAMPLE

Pre-forming of the catalyst 550 g of toluene freed from oxygen are initially introduced into a glass receiver under a nitrogen atmosphere, and 0.249 g (0.95 mmol) of triphenylphosphine and 0.19 mmol of rhodium in the form of Rh 2-ethylhexanoate are added, while stirring. The resulting toluene solution is transferred under a nitrogen atmosphere into a 5 l autoclave, with a stirrer, which has been flushed thoroughly with nitrogen. A pressure of 270 bar [27 MPa] is established by forcing in synthesis gas, while stirring, and the mixture is heated up to 125° C. and allowed to react for 2 hours. This completes the pre-forming of the catalyst.

Hydroformylation

When the pre-forming has ended, a total of 1300 g of propylene are pumped from a pressurized receiver into the autoclave under a pressure of 270 bar [27 MPa] at 125° C. in the course of 1.5 hours. The pressure is kept at 270 bar by forcing in synthesis gas. The reaction temperature is 125° C., the excess heat released by the hydroformylation being removed by means of cooling (air fan). The hydroformylation proceeds in the presence of 15 ppm of rhodium, based on the total propylene employed. The ratio of triphenylphosphine to rhodium is 5:1 (corresponding to a ratio of P:Rh=5:1). After the end of pumping, the mixture is allowed to after-react for another hour, and the autoclave is then cooled and let down in the course of 1.5 hours.

The contents of the autoclave are emptied under the remaining residual pressure into a 6 l three-necked flask with immersion connectors and weighed (1704 g). A propylene conversion of 59% is calculated from the weight increase.

For comparison, the reaction conditions and the results of Example 1 using 1,4-bis[bis(4-dimethylaminophenyl)phosphino]butane×2 palmitic acid and of the Comparison Example using triphenylphosphine are summarized in the following table.

TABLE

Hydroformylation of propylene

|  | Example 1 | Comparison Example |
|---|---|---|
| Propylene | 1300 g | 1300 g |
| Pumping-in time | 1.5 h | 1.5 h |
| Rh* | 15 ppm | 15 ppm |
| Temperature | 125° C. | 125° C. |
| Pressure** | 270 bar | 270 bar |
| P:Rh | 5:1 | 5:1 |
| Reaction product | 2630 g | 1704 g |
| n:i ratio*** | 62:38 | 60:40 |
| Conversion (based on propylene) | 92% | 59% |

*based on total propylene employed
**$CO/H_2$
***n-butanal:i-butanal

We claim:

1. A process for the preparation of an aldehyde, which comprises reacting an olefinic compound having 2 to 20 carbon atoms with carbon monoxide and hydrogen, in the presence or absence of a solvent, in the presence of a catalyst comprising rhodium and a compound or a mixture of compounds of the formula (I)

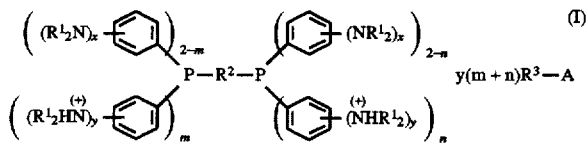

in which $R^1$ is H or an alkyl radical having 1 to 12 carbon atoms, $R^2$ is a straight-chain alkylene radical having 1 to 8 carbon atoms, an oxygen-containing alkylene radical having 2 to 4 carbon atoms, a radical of the formula (II) or (III)

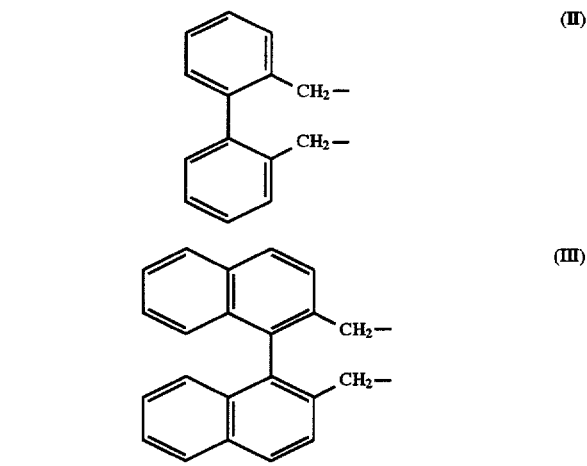

or a cycloalkylene radical having 3 to 10 carbon atoms, $R^3$ is an alkyl radical having 1 to 25 carbon atoms or an aryl radical having 6 to 10 carbon atoms, A is a radical $—COO^-$ or $—SO_3^-$ and x=0, y=1, m=1 and n=1, or x=1, y=1, m=(1 or 2) and n=(1 or 2), or, if $R^2$ is a radical of the formula (II) or (III), x=1, y=0, m=(0 or 1) and n=(0 or 1), at a temperature from 50° to 190° C. and under a pressure from 0.1 to 45 Mpa, and separating the reaction product off from the catalyst.

2. The process as claimed in claim 1, wherein a compound of the formula (I) in which x=0, y=1, m=1 and n=1, or x=1, y=1, m=(1 or 2) and n=(1 or 2), or a mixture of these compounds, is employed.

3. The process as claimed in claim 1, wherein a compound of the formula (I) in which x=1, y=1, m=(1 or 2) and n=(1 or 2), or a mixture of these compounds, is employed.

4. The process as claimed in claim 1, wherein a compound of the formula (I) in which the $R^1_2N-$ and $R^1_2NH^+$-group are in the meta- or para-position relative to the bond which joins the benzene ring to the particular P atom, or a mixture of these compounds, is employed.

5. The process as claimed in claim 1, wherein a compound of the formula (I) in which $R^1$ is an alkyl radical having 1 to 4 carbon atoms or a mixture of these compounds, is employed.

6. The process as claimed in claim 1, wherein a compound of the formula (I) in which $R^2$ is an alkylene radical having 1 to 4 carbon atoms or a radical $—(CH_2)_2—O—(CH_2)_2—$ or a mixture of these compounds, is employed.

7. The process as claimed in claim 1, wherein a compound of the formula (I) in which $R^3$ is an alkyl radical having 12 to 24 carbon atoms or an aryl radical having 6 to 7 carbon atoms or a mixture of these compounds, is employed.

8. The process as claimed in claim 1, wherein a compound of the formula (I) in which A is a radical $—COO^-$ or a mixture of radicals $—COO^-$.

9. The process as claimed in claim 1, wherein the reaction is carried out in the presence of 5 to 500 ppm of rhodium, based on the olefinic compound.

10. The process as claimed in claim 1, wherein the compound of the formula (I) and rhodium are employed in a ratio of 1:1 to 200:1 (mol of compound of the formula (I) per g atom of rhodium).

11. The process as claimed in claim 1, wherein said olefinic compound is a substituted or unsubstituted alkene having 2 to 20 carbon atoms, a substituted or unsubstituted diene having 4 to 10 carbon atoms, a substituted or unsubstituted cycloalkene or dicycloalkene having 5 to 12 carbon atoms in the ring system, an ester of an unsaturated carboxylic acid having 3 to 20 carbon atoms and an aliphatic alcohol having 1 to 18 carbon atoms, an ester of a saturated carboxylic acid having 2 to 20 carbon atoms and an unsaturated alcohol having 2 to 18 carbon atoms, an unsaturated alcohol or ether having in each case 3 to 20 carbon atoms or an araliphatic olefin having 8 to 20 carbon atoms.

12. The process as claimed in claim 1, wherein said olefinic compound is dicyclopentadiene.

13. The process as claimed in claim 1, wherein the reaction is carried out at a temperature of 80° to 180° C.

14. The process as claimed in claim 1, wherein the reaction is carried out under a pressure of 1 to 35 MPa.

15. The process as claimed in claim 1, wherein the reaction mixture is separated off from the catalyst by means of distillation, extraction or pressure filtration.

16. The process as claimed in claim 1, wherein the reaction mixture is separated off from the catalyst by means of a semi-permeable membrane.

17. The process as claimed in claim 16, wherein said membrane is a polyamide membrane.

18. The process as claimed in claim 16, wherein said membrane is a polyaramid membrane.

19. The process as claimed in claim 3, wherein the compound of the formula (I) in which the $R^1_2N$- and the $R^1_2HN^+$-group are in the para-position, relative to the bond which joins the benzene ring to the particular P atom and $R^1$ is a methyl or ethyl radical, $R^2$ is trimethylene or tetramethylene radical, $R^3$ is an alkyl radical having from 14 to 22 carbon atoms and the reaction is carried out in the presence of 10 to 150 ppm of rhodium, based on the olefinic compound and the reaction is carried out at a temperature of 100° to 170° C. with a pressure of 3 to 30 Mpa.

20. The process as claimed in claim 19, wherein $R^1$ is a methyl radical and the compound of the formula (I) and rhodium are employed in a ratio of 2:1 to 10:1 (mol of compound of the formula (I) per g atom of rhodium).

* * * * *